United States Patent
Cherek et al.

(10) Patent No.: US 7,170,967 B2
(45) Date of Patent: Jan. 30, 2007

(54) METHOD AND DEVICE FOR POSITIONING A PATIENT IN A MEDICAL DIAGNOSIS DEVICE OR THERAPY DEVICE

(75) Inventors: Dieter Cherek, Hirschaid (DE); Robert Kagermeier, Nürnberg (DE); Michael Loser, Erlangen (DE); Donal Medlar, Weisendorf (DE); Hendrik Steinmann, Worms (DE); Uwe Urmoneit, Gerhardshofen (DE)

(73) Assignee: Siemens Aktiengsellschaft, Munich (DE)

( * ) Notice: Subject to any disclaimer, the term of this patent is extended or adjusted under 35 U.S.C. 154(b) by 683 days.

(21) Appl. No.: 10/623,343

(22) Filed: Jul. 18, 2003

(65) Prior Publication Data

US 2004/0082852 A1    Apr. 29, 2004

(30) Foreign Application Priority Data

Jul. 18, 2002   (DE) ............................... 102 32 681

(51) Int. Cl.
   *H05G 1/60*   (2006.01)
   *H05G 1/00*   (2006.01)

(52) U.S. Cl. ........................ 378/20; 378/208

(58) Field of Classification Search ............. 378/20, 378/195, 205–208; 250/363.02, 363.03, 250/363.04

See application file for complete search history.

(56) References Cited

U.S. PATENT DOCUMENTS

| | | | | |
|---|---|---|---|---|
| 5,622,187 | A | * | 4/1997 | Carol ........................ 128/897 |
| 5,727,554 | A | * | 3/1998 | Kalend et al. ............. 600/587 |
| 6,272,368 | B1 | * | 8/2001 | Alexandrescu ............ 600/407 |
| 6,405,072 | B1 | * | 6/2002 | Cosman ..................... 600/426 |
| 2002/0044631 | A1 | * | 4/2002 | Graumann et al. ......... 378/205 |

* cited by examiner

*Primary Examiner*—Edward J. Glick
*Assistant Examiner*—Irakli Kiknadze
(74) *Attorney, Agent, or Firm*—Schiff Hardin LLP

(57) ABSTRACT

In a method and a device for positioning a patient in a medical diagnosis device or therapy device having a position calculating device and a patient bed adjustable in at least one plane, at least one optical target marking is brought into conformity with a body region of the patient. At least one image recording device is used for obtaining an exterior image of the patient that is displayed on a screen. The target marking that is spatially coupled with the coordinate system of the diagnosis device or therapy device, is superimposed on the image of the patient on the screen such that a predetermined body region of the patient can be brought into a desired spatial correlation with the target marking by remote control movement of the patient bed.

22 Claims, 1 Drawing Sheet

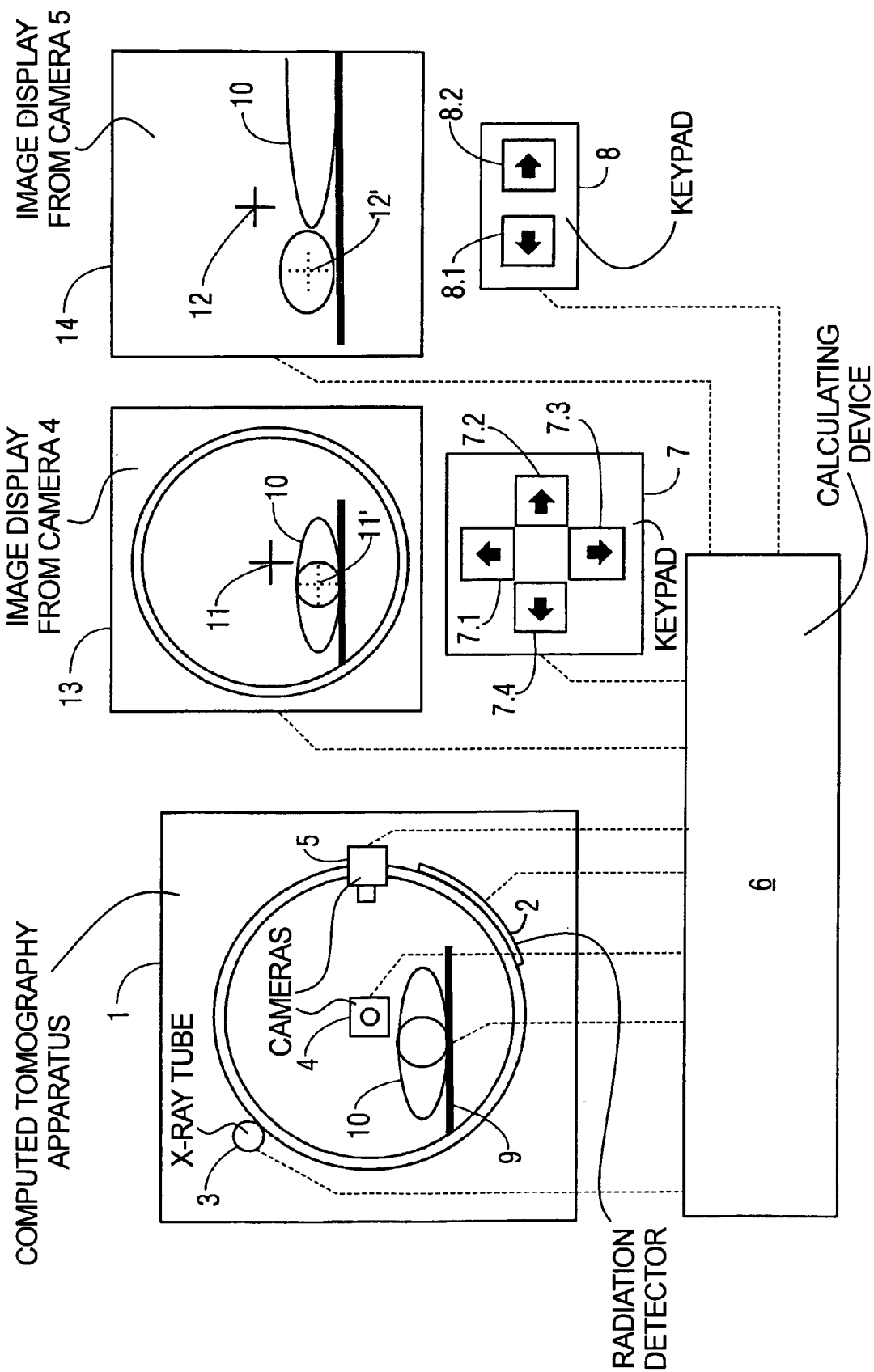

METHOD AND DEVICE FOR POSITIONING A PATIENT IN A MEDICAL DIAGNOSIS DEVICE OR THERAPY DEVICE

BACKGROUND OF THE INVENTION

1. Field of the Invention

The present invention concerns a method and a device for positioning a patient in a medical diagnosis device or medical therapy device (medical device) of the type having a position calculating unit and a patient bed that is adjustable in at least one plane, and at least one image recording device that obtains an image of the exterior of the patient and graphically reproduces the image on a screen.

2. Description of the Prior Art

Methods and devices of the above general type are commonly known. The patient is normally manually arranged using laser beam localizers or light beam localizers, for example in a CT installation, and the CT table is manually controlled at the location of the patient to place the patient in the appropriate position. For example, the vertical centering of the center of the patient's head in the rotational center of the CT x-ray tube is implemented in this manner.

Such a method and corresponding device requires time-consuming manual operation by the operating personnel with interactions by the operating personnel directly with the patient that sometimes are disturbing and requires the operator to interact with the operating console of the diagnosis device or therapy device. This is particularly disadvantageous during survey examinations, in which a number of patients should be guided through such a diagnosis device in the shortest possible amount of time.

SUMMARY OF THE INVENTION

It is an object of the present invention to provide a method and a device for positioning a patient in a medical diagnosis or therapy device which allow the positioning of the patient to be implemented in less time, possibly with fewer personnel.

This object is achieved according to the invention in which a method and device wherein manual operation and interactions between the operating personnel and the patient are reduced by displaying an image of the patient with spatial correlation to the diagnosis device or therapy device, and wherein a target marking which is only identifiable on the screen is brought into conformity with a desired body region of the patient by remote control movement of the patient bed.

A target marking is superimposed on the image of the patient on the screen, without it being necessary to additionally project this target marking onto the patient (as is normal in the prior art), such that the patient can be moved until the position of a predetermined body region is brought into coincidence in the desired position, with the target marking (virtually applied on the screen) that is in a known spatial correlation to the coordinate system of the diagnosis device or therapy device.

In the inventive method for positioning a patient in a medical diagnosis device or therapy device having a position calculating device and a patient bed that is adjustable in at least one plane, at least one optical target marking is brought into conformity with a body region of the patient. An improvement is inventively achieved by using at least one image recording device for imaging the exterior of the patient on a screen, with the spatial correlation between the coordinate system of the diagnosis device or therapy device and the acquired image being known, and on the screen at least one target marking, that is spatially coupled with the coordinate system of the diagnosis device or therapy device, is superimposed with the image of the patient, such that a predetermined body region of the patient can be brought into a desired spatial correlation with the target marking by remote controlled movement of the patient bed.

Such a target marking can be, for example, a simple target symbol or cross-hair symbol, or a display of an actual scan region of the diagnosis device or therapy device.

If the patient is imaged in the direction of the rotational axis of a computed tomography apparatus, for example, the target marking can display the rotational center of the computed tomography apparatus.

To achieve a further improvement with the inventive method, instead of an image-recording device that solely enables the patient to be positioned in a plane, at least two image recording devices can be used with respective recording axes that are independent of one another, preferably orthogonal to one another. It is thus possible to move the patient in 3-dimensional space in the desired position, corresponding to the basic method described above.

The movement of the patient or the movement of the patient bed can ensue via a remote control, preferably connected to a joystick or directional keys on the console of the diagnosis device or therapy device.

Naturally, there is also the possibility to use the movement of a mouse or trackball coupled to an indicator on the screen in order to move the patient into the desired position.

If a number of image recording devices or cameras are used, it can be advantageous to use different target markings. For example, a cross-hair symbol can be used to display the rotational axis for an image recording device whose direction of recording is arranged in the direction of the axis of rotation of a CT device, while the currently implemented scan region of a computed tomography apparatus can be used as target marking for an image recording device which images the patient from above. Likewise, the CT slice plane also can be displayed in order to enable display of the position of the individual slices in the preparatory stage of the CT procedure, and to enable undertaking, as needed, a corresponding correction of the patient position.

In accordance with the invention, in addition to the target marking, a desired final position of the target marking can be marked on the image of the patient on the screen using an appropriate input device, preferably a mouse or a joystick, and subsequently an automatic controller can move the patient bed until congruence is reached between the target marking and the desired position of the target marking.

An inventive device for positioning a patient in a medical diagnosis device or therapy device for implementation of the inventive method, has a position calculating unit and a patient bed that is adjustable in at least one plane, and at least one target marking is provided that is to be brought into correspondence with a defined body region of the patient, and at least one image recording device and a screen to display the patient image. A processor superimposes at least one target marking that is spatially coupled with the coordinate system of the diagnosis device or therapy device, on the patient image on the screen such that a predetermined body region of the patient can be can be brought into a desired spatial correlation with a target marking by movement of the patient bed.

The target marking can be, for example, a target cross which preferably corresponds to the rotational center of a computer tomography device. Alternatively, borderlines of the implemented scan region or markings for the scanned slice planes also can be displayed.

If a 3-dimensional positioning of the patient is needed, at least two image-recording devices are necessary, and their recording axes must be oriented independently of one another, preferably orthogonal to one another.

Each movement plane of the patient bed can have an associated image-recording device with a recording axis arranged perpendicular to this movement plane. In addition, at least one image recording device can be provided with a 3D scanner, preferably with a laser scanner or a 3D CMOS sensor.

Corresponding to the spatial detection, the patient image displayed on the screen can also render a spatial display, and this must be viewed as needed with appropriate 3D glasses by the operating personnel.

In a preferred embodiment, the inventive device allows a desired final position of the target marking to be entered into image of the patient on a screen in addition to a the target marking, using an input device (preferably a mouse or joystick). Furthermore, an automatic controller can be provided that moves the patient bed until a convergence is achieved between the target marking and the desired position of the target marking. Using this embodiment of the inventive device, it is possible to effect an automatic positioning of the patient with a minimum of operator effort solely by indicating the desired position of the target marking, with the calculating unit computing a correlation between the additional existing target marking and the desired position of the target marking and controlling movement of the patient bed in the appropriate manner in order to bring both these markings into congruence. It is understood that this can ensue not only in a single plane, but rather also 3-dimensionally, using two graphical displays of the patient that are detected by image recording devices that have respective recording axes that are mathematically independent from one another.

It should be noted that the functional means described above primarily are programs or program modules that define the operation of the calculating unit of the diagnosis device or therapy device, including the controller of the patient bed.

DESCRIPTION OF THE DRAWINGS

The single FIGURE is a schematic representation of an inventive computed tomography system shown in section.

DESCRIPTION OF THE PREFERRED EMBODIMENTS

The computed tomography system 1 shown in the drawing has an x-ray source 3 in the rotatable gantry and a detector 2 positioned opposite it that is mounted to the gantry such that it can be rotated around a rotational axis. A bed 9 with a patient 10 located thereon is schematically shown inside the gantry. Additionally, the section shows two video cameras 4 and 5. The first video camera 4 is arranged with its recording axis coaxial to the rotational axis of the gantry, and this records the patient 10 from the head. The second video camera 5 is arranged laterally to the patient 10, such that its recording axis is perpendicular to the rotational axis of the gantry.

The two recordings (images) of the video cameras 4 and 5 are shown in the image displays 13 and 14. The image display 13 shows the recording of the patient 10 in the gantry, with a target marking 11 in the form of a cross-hair symbol being inventively superimposed on the image of the patient 10 positioned in the gantry. The target marking 11 shows the additional rotational center of the gantry and signifies that the patient 10 is positioned at this point in time beneath the rotational center. The patient bed 9 can be moved by the operating personnel by remote control with the keys 7.1 through 7.4 of the keypad 7 until the patient 10 exhibits the correct position in relation to the displayed cross-hair symbol in the displayed plane.

The patient 10 is displayed sideways to the position of the camera 5 in the image display 14, and again movement of the patient bed 9, and therewith the patient 10, is enabled by the keys 8.1 and 8.2 of the keypad 8. The patient 10 is still not located in the final correct position. By pressing the keys 8.1 and 8.2 of the controller of the patient bed, the patient 10 can be guided to the desired position by the operating personnel.

As an alternative to the manual movement of the patient bed 9 and the patient 10 by key operation, the screen itself can be marked with the location of the patient 10 that should finally be in conformity with the target marking. The patient bed 10 can be automatically moved by the calculating device 6 of the computed tomography system 1 on the basis of the knowledge of the position of the target marking, the input of the desired end position of the target marking, and the translation conditions necessary, until a conformity between the center of the cross-hair symbols 11 and 12 and the target point applied by the operating personnel is achieved.

With the inventive device, the patient 10 can be positioned in a simple manner in the desired position, without light markings or other marking having to be made on the patient himself or herself.

The inventive method and device can be used not only with x-ray computed tomography systems, but also with magnetic resonance tomography systems, angiography devices, ultrasound therapy devices, or radiation therapy devices.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for positioning a patient in a medical device comprising the steps of:

obtaining an image of an exterior of a patient disposed on a patient bed that is movable in at least one plane relative to a medical device, said medical device having an associated coordinate system;

displaying said image on a display screen;

via a calculating unit connected to said display screen, in which a spatial correlation between the coordinate system of the medical device and said image is known, causing a target marking, spatially coupled with said coordinate system of said medical device, to be superimposed on said image on said display screen; and remotely controlling movement of said patient bed through said calculating unit to bring a predetermined body region of the patient in the image on the display screen into a desired spatial correlation with said target marking on said display screen.

2. A method as claimed in claim 1 wherein said medical device has a scan region, and comprising using an image of said scan region of said medical device as said target marking.

3. A method as claimed in claim 1 comprising employing a symbol selected from the group consisting of a target symbol and a cross-hair symbol as said target marking.

4. A method as claimed in claim 1 wherein said medical device has a rotational center, and employing a designation of said rotational center as said target marking.

5. A method as claimed in claim 1 comprising obtaining and displaying at least two images of the exterior of the patient respectively obtained relative to recording axes that are independent of each other and viewing said at least two images simultaneously with said target marking superimposed thereon.

6. A method as claimed in claim 5 comprising obtaining said at least two images along respective recording axes that are orthogonal to each other.

7. A method as claimed in claim 5 wherein said patient bed is movable in a plurality of planes and, for each plane, acquiring an image of the exterior of the patient along a recording axis perpendicular to that plane.

8. A method as claimed in claim 1 comprising remotely controlling movement of the patient bed through said calculating unit using a manually operable input device connected to said calculating unit.

9. A method as claimed in claim 1 comprising manually entering, into said calculating unit, a designation of a body region of the patient to be examined and automatically generating, in said calculating unit, said target marking to designate said body region.

10. A method as claimed in claim 1 comprising obtaining at least two images of the exterior of the patient along respective image acquisition axes that are independent of each other, displaying each of said images, and superimposing different target markings in the displayed images.

11. A method as claimed in claim 1 comprising manually entering, through said calculating unit, a selected final position of said target marking on said display screen relative to said image on said display screen, and automatically controlling movement of said patient bed, through said calculating unit, to bring said patient on said patient bed to said final position.

12. An arrangement for positioning a patient in a medical device comprising:
- a patient bed, adapted to receive a patient thereon, that is movable in at least one plane relative to a medical device, said medical device having an associated coordinate system;
- an image recording device for obtaining an image of an exterior of the patient on the bed;
- a display screen on which said image is displayed;
- a calculating unit connected to said display screen, in which a spatial correlation between the coordinate system of the medical device and said image is known, which superimposes a target marking, spatially coupled with said coordinate system of said medical device, on said image on said display screen; and
- a remote controller for remotely controlling movement of said patient bed through said calculating unit to bring a predetermined body region of the patient in the image on the display screen into a desired spatial correlation with said target marking on said display screen.

13. An arrangement for positioning a patient as claimed in claim 12 wherein said medical device has a scan region, and wherein said calculating unit superimposes an image of said scan region of said medical device on said display screen as said target marking.

14. An arrangement for positioning a patient as claimed in claim 12 wherein said calculating unit superimposes a symbol selected from the group consisting of a target symbol and a cross-hair symbol on said display screen as said target marking.

15. An arrangement for positioning a patient as claimed in claim 12 wherein said medical device has a rotational center, and employing a designation of said rotational center as said target marking.

16. An arrangement for positioning a patient as claimed in claim 12 wherein said image recording device is a first image recording device and wherein said image is a first image, and wherein said arrangement comprises a second image recording device for obtaining a second image of the exterior of the patient on the bed relative to a recording axis that is independent of a recording axis of said first image recording device, and wherein a spatial correlation between the coordinate system of the medical device and said second image is known in said calculating unit, and wherein said calculating unit superimposes said target marking in said first and second images, which are simultaneously displayed on said display screen.

17. An arrangement for positioning a patient as claimed in claim 16 wherein said first and second image acquisition devices have respective recording axes that are orthogonal to each other.

18. An arrangement for positioning a patient as claimed in claim 12 wherein said patient bed is movable in a plurality of planes, and wherein said arrangement comprises, for each plane, an image recording device for recording an image of the exterior of the patient along a recording axis perpendicular to that plane, and wherein a spatial correlation between the coordinate system of the medical device and each of said images is known in said calculating unit, and wherein said calculating unit superimposes said target marking in each of said images on said display screen.

19. An arrangement for positioning a patient as claimed in claim 12 wherein said remote controller comprises a manually operable input device connected to said calculating unit for remotely controlling movement of the patient bed through said control unit.

20. An arrangement for positioning a patient as claimed in claim 12 comprising an input unit for allowing manual entry, into said calculating unit, of a designation of a body region of the patient to be examined and wherein said calculating unit automatically generates said target marking to designate said body region.

21. An arrangement for positioning a patient as claimed in claim 12 wherein said image acquisition device is a first image acquisition device and wherein said image is a first image, and wherein said arrangement comprises a second image acquisition devices for obtaining a second image of the exterior of the patient, said second image being displayed on said display screen, and wherein a spatial correlation between the coordinate system of the medical device and said second image is known in said calculating unit, and wherein said calculating unit superimposes respectively different target markings, spatially coupled with said coordinate system of said medical device, on said first and second images on said display screen.

22. An arrangement for positioning a patient as claimed in claim 12 comprising an input unit allowing manual entry, through said calculating unit, of a selected final position of said target marking on said display screen relative to said image on said display screen, and wherein said calculating unit comprises said remote controller and automatically controls movement of said patient bed, to bring said patient on said patient bed to said final position.

* * * * *